United States Patent
Hardinghaus et al.

(10) Patent No.: US 7,001,582 B2
(45) Date of Patent: Feb. 21, 2006

(54) MICRONIZED BARIUM SULFATE

(75) Inventors: Ferdinand Hardinghaus, Bad Hoenningen (DE); Tanja Engels, Sankt Katharinen (DE); Jai-Won Park, Goettingen (DE); Karl Koehler, Diekholzen (DE); Hans Gabel, Kasbach-Ohlenberg (DE); Joerg Glas, Rheinbrohl (DE)

(73) Assignee: Solvay Barium Strontium GmbH, Hannover (DE)

( * ) Notice: Subject to any disclaimer, the term of this patent is extended or adjusted under 35 U.S.C. 154(b) by 0 days.

(21) Appl. No.: 10/823,555

(22) Filed: Apr. 14, 2004

(65) Prior Publication Data

US 2004/0197262 A1   Oct. 7, 2004

Related U.S. Application Data

(63) Continuation of application No. 10/305,400, filed on Nov. 27, 2002, now abandoned, which is a continuation of application No. PCT/EP01/06031, filed on May 26, 2001.

(30) Foreign Application Priority Data

May 31, 2000 (DE) ............................ 100 26 791

(51) Int. Cl.
   *C01F 11/46*   (2006.01)

(52) U.S. Cl. ............. 423/554; 106/461; 424/401
(58) Field of Classification Search ............ 423/166, 423/554; 106/461; 424/401
    See application file for complete search history.

(56) References Cited

U.S. PATENT DOCUMENTS

| 2,358,050 | A | * | 9/1944 | Boulet ..................... 423/554 |
| 4,894,093 | A | * | 1/1990 | Aderhold et al. ........... 106/461 |
| 5,171,572 | A | * | 12/1992 | Suganuma et al. ......... 424/401 |
| 5,246,687 | A | * | 9/1993 | Gorre, deceased et al. . 423/554 |
| 5,340,582 | A | * | 8/1994 | Sugasawa et al. .......... 424/401 |
| 5,580,377 | A | * | 12/1996 | Ohtsu et al. ............... 106/461 |
| 5,976,511 | A | * | 11/1999 | Ohtsu et al. ............... 424/59 |
| 5,997,775 | A | * | 12/1999 | Hayashi et al. .......... 252/518.1 |

FOREIGN PATENT DOCUMENTS

| GB | 2134094 | * | 8/1984 |
| WO | 01/92157 | * | 12/2001 |

* cited by examiner

*Primary Examiner*—Wayne A. Langel
(74) *Attorney, Agent, or Firm*—Crowell & Moring LLP

(57) ABSTRACT

Micronized barium sulfate ($BaSO_4$) and methods for the production and use thereof. The micronized barium sulfate of the invention is particularly suitable for use as an additive or filler for adhesives, colorants, rubber articles and/or cosmetics.

17 Claims, No Drawings

MICRONIZED BARIUM SULFATE

CROSS REFERENCE TO RELATED APPLICATIONS

This application is a continuation of U.S. patent application Ser. No. 10/305,400, filed Nov. 27, 2002, abandoned, which in turn is a continuation of international patent application No. PCT/EP01/06031, filed May 26, 2001 designating the United States of America and published in German as WO 01/92157, the entire disclosure of which is incorporated herein by reference. Priority is claimed based on Federal Republic of Germany patent application No. DE 100 26 791.2, filed May 31, 2000.

BACKGROUND OF THE INVENTION

The present invention relates to a particulate barium sulfate, its production, and its use.

Barium sulfate may be used as a pigment in paper production, for example. Other intended applications, such as an additive for cosmetics like skin creams and sunscreens, or as a filler in pigments, adhesives, or rubber articles, however, require extremely fine particles of $BaSO_4$.

SUMMARY OF THE INVENTION

An object of the present invention is to provide a new effective method for producing a finely dispersed, particulate micronized barium sulfate.

Another object of the invention is to provide an improved micronized barium sulfate which may be used as an additive for cosmetics or as filler for pigments, adhesives, or rubber articles.

These and other objects are achieved in accordance with the present invention by providing a method for producing particulate barium sulfate in which at least 90% of the particles have a primary grain diameter of less than 0.1 $\mu$m, said method comprising combining a barium salt solution with an alkali sulfate salt solution to form a reaction mixture in a continuously operating mixing reactor, in which shear, displacement and frictional forces of intermeshing tools act at high relative speed on the reaction mixture formed, whereby resulting barium sulfate is precipitated, and after passage of the reaction mixture through the reactor, separating and drying the resulting barium sulfate; wherein the concentration of barium salt and sulfate in the salt solutions is at least 80% of the maximum possible concentration.

In accordance with a further aspect of the invention, the objects are achieved by providing a particulate, coated BaSO4, wherein at least 95% of the particles, preferably 99% of the particles, and particularly preferably 100% of the particles, have a primary grain diameter $\leq 0.1$ $\mu$m, produced according to the method of the invention.

The method according to the present invention for producing particulate barium sulfate provides that a barium salt solution is combined with a sulfate salt solution in a continuously operating mixing reactor, in which shear, transverse, and frictional forces of intermeshing tools act in accordance with the rotor-stator principle, with high relative speed on the reaction mixture formed, and after the reaction mixture has passed through the reactor, the resulting barium sulfate is separated out and dried, subject to the condition that the concentration of barium salt and/or sulfate corresponds to at least 80%, preferably at least 90%, of the maximum possible concentration. The shear, transverse, and frictional forces in the reactor have the effect that the barium sulfate is produced in extremely finely dispersed form.

In principle, any arbitrary aqueous barium salt solution having a correspondingly high concentration may be used. In the context of the present invention, barium hydroxide is also understood as a salt that may be used. A barium chloride ($BaCl_2$) solution is the most technically expedient. The concentration of barium salt in the solution advantageously corresponds to at least 95% of the maximum possible concentration. For $BaCl_2$, this is approximately at least 0.9 mole/liter at 60° C.

As used herein the term "sulfate solutions" includes solutions of any arbitrary aqueous sulfate salt. In the context of the present invention, sulfuric acid is also considered a "sulfate solution." The concentration is preferably at least 95% of the maximum possible concentration, up to the saturation limit. Aqueous alkali sulfate solution is preferably used. Alkali preferably stands for sodium. The concentration of $Na_2SO_4$ (at 40° C.) is preferably at or above 0.5 mole/liter, up to saturation concentration.

When the method according to the present invention is carried out, micronized barium sulfate is obtained in which at least 90% of the particles have a primary grain diameter smaller than 0.1 $\mu$m, preferably at least 95%, particularly preferably 99%, very particularly preferably 100%.

Devices in which the rotor rotates at a high speed are highly suitable for use in the method of the invention. The rotor speed is preferably 2000 to 8000 rotations/sec. The residence time of the reaction mixture in the mixing and homogenization device is preferably in the millisecond range.

The grain size was assessed via microscopic imagery.

Before drying, which may advantageously be carried out at a temperature in the 100 to 120° C. range, the $BaSO_4$ separated out after passing through the reactor may be washed one or more times with water. If barium hydroxide/sulfuric acids are used, this has the advantage that no foreign salts (e.g., NaCl) arise.

The precipitation of barium sulfate advantageously may be carried out at a temperature in the 0 to 100° C. range, preferably between 20° C. to 50° C.

Depending on the intended application, a slight excess of sulfate (up to 5%) may be advantageous.

According to one embodiment of the method of the invention, agents that influence the crystallization or the surface properties are not added.

A further object of the present invention is the particulate barium sulfate that is obtainable through the method put forth in the present invention, in which at least 90% of the primary grain particles have a diameter in the range of less than 0.1 $\mu$m, and which is free of precipitating agents.

The $BaSO_4$ obtainable according to the present invention in this way may be used for all purposes for which $BaSO_4$ is typically used. It is particularly useful as a filler for cosmetics (it also has reflective, scattering, and light refracting effects). For this purpose, it is used in appropriate formulations, for example as a cream. The formulations obtained in this way, which may be used as sunscreen, for example, are superior to formulations having $TiO_2$ as a pigment (UV-light protective agent), since no visible residues remain after absorption into the skin. If desired, a sunscreen may be introduced; in this way, the sun protection factor may be individually adjusted in accordance with its quantity, and the cream and/or formulation is usable as a sunscreen.

The BaSO$_4$ obtainable according to the present invention is also distinguished by a significant improvement of the skin feel.

According to another embodiment, a wetting or dispersing agent is added to the barium sulfate. This may be performed during the precipitation, after the precipitation, or both during and after the precipitation. The wetting and/or dispersing agent leads to the formation of small crystals, which agglomerate as little as possible. The wetting and/or dispersing agent also influences the surface properties of the barium sulfate, i.e., the product obtained is a coated product.

Dispersing agents or wetting agents for aqueous and non-aqueous systems are usable. The dispersing agent is selected so that it is compatible in regard to the intended use. Hydrophilic dispersing agents are advantageously used when this property is desirable, if the base materials of the adhesive, the pigment, or the cosmetic are also hydrophilic. Otherwise, appropriate hydrophobic dispersing agents are selected. Therefore, a tailored adjustment to the desired technical application properties is possible through the coated particles according to the present invention, having adjustable surface properties.

Highly useful dispersing agents in the context of the present invention include (short chain) polyacrylates, typically in the form of the sodium salt; polyethers such as polyglycol ether; ether sulfonates such as lauryl ether sulfonate in the form of the sodium salt; esters of phthalic acid and its derivatives; esters of polyglycerol; amines such as triethanolamine; and esters of fatty acids such as stearic acid ester.

The quantity of dispersing agent is flexible. A very fine product having a very high surface area is achieved at a content of up to 3 weight-percent of the dispersing agent, in relation to the total weight of dry product. Barium sulfate having a content of 3 weight-percent sodium polyacrylate has, for example, a surface area of 48 m$^2$/g; the average particle diameter, determined via wide angle x-ray diffraction in accordance with modified Warren-Averbach analysis, was 30 nm in the primary grain. Without adding dispersing agents, surface areas of 20 m$^2$/g were achieved. The dispersing or wetting agent content in the finished product is advantageously 1 to 3 weight-percent on a dry mass basis.

As noted above, a barium sulfate obtained using a wetting or dispersing agent is also an object of the present invention.

If the dispersing agent or wetting agent is added after the precipitation, it is advantageous to knead it into the freshly precipitated barium sulfate "dough," for example through corresponding kneading apparatus or extruders having mixing sections or something similar. This is also true if dispersing agent is to be worked in during and after the precipitation.

The resulting coated barium sulfate, which is redispersable into particles having a particle size below 100 nm, preferably below 50 nm, is particularly suitable for use as a filler for adhesives (such as reactive, melt, and dispersion adhesives), for rubber articles, for pigments (such as coating varnish, base varnish, or primer) and for cosmetics (such as for the purpose of UV absorption, or for skin care or lip care products).

The coated barium sulfate is inert, transparent, and provides rheological properties advantageous to the application matrix. It is redispersable in solvents and/or the base materials for adhesives, pigments, cosmetics, or rubber articles. Through selection of the suitable dispersing agent, it is also compatible with the material used. The tailored coating adjustment is therefore easily possible.

The following examples are intended to illustrate the present invention in further detail, without limiting its scope.

EXAMPLE 1

Preparation of Sub-micron BaSO$_4$ Without a Dispersing Agent

A mixing reactor having a rotor with a speed of 6,650 rpm was used; the rotor exerted corresponding shear, displacement and frictional forces on the mixture of the reactants.

Sodium sulfate solution (40° C., 0.96 mole/liter, 400 liters/hour) and barium chloride solution (15° C., 0.96 mole/liter, approximately 400 liters/hour) were each introduced into the mixing reactor using a metering pump. The suspension exiting from the mixing reactor was filtered, washed using demineralized water, dried at 110° C. in a drying cabinet, and deagglomerated. Virtually 100% of the particles had a primary grain diameter <0.1 μm.

EXAMPLE 2

Preparation of a Vanishing Cream Having 5 Weight-percent BaSO$_4$ Added 2.1 Preparation of a Base Material for an Oil/water Type Vanishing Cream

| | | |
|---|---|---|
| a) | Lanette N$^R$ | 3.0% |
| | Stearin | 9.0% |
| | Vitamin F ethyl ester | 3.0% |
| | Carrot oil | 3.0% |
| | Arnica oil | 3.0% |
| | Preservative (Phenonip ™) | 0.5% |
| b) | H$_2$O, distilled | 74.5% |
| | Miglyol ™ | 4.0% |
| | Triethanolamine | 0.5% |

Melt a) and heat to approximately 80° C. Heat b) to approximately 80° C. and add to part a) while stirring. Stir further using dissolver (rapid stirrer), until the emulsion is cooled to approximately 40° C. (approximately 1 hour, 15 minutes). The resulting vanishing cream is creamy and absorbs into the skin without residues.

2.2 Adding the BaSO$_4$

After the heated components listed under 2.1 b) were added to the components listed under 2.1 a), blanc fixe (BaSO$_4$) produced according to example 1 was added while stirring. The quantity added was 5 weight-percent BaSO$_4$, in relation to the base material from example 1, set as 100 weight-percent.

This cream, which contained BaSO$_4$, was also creamy and absorbed into the skin without residues. There was also no formation of agglomerates to be detected.

By adding a precisely calculated quantity of a sunscreen, the sun protection factor may be individually adjusted. The cream is then also usable as a sunscreen.

EXAMPLE 3

Preparation of Coated BaSO$_4$

Example 1 was repeated. The Na$_2$SO$_4$ solution, however, had sodium polyacrylate (product Dispex N40, Ciba) added to it. The quantity was selected in such a way that 3 weight-percent of the dispersing agent was contained in the finished dried product.

The resulting coated barium sulfate had a specific surface area of 48 m$^2$/g (BET method) and an average particle diameter of 30 nm (wide angle x-ray diffractometry, modified Warren-Averbach method) in the primary grain (measurement without redispersion).

This product is particularly suitable for use as an additive for pigments, rubber articles, and adhesives, because the dispersing agent acts as a binding mediator.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A method for producing particulate barium sulfate in which at least 90% of the particles have a primary grain diameter of less than 0.1 μm, said method comprising:
   combining a barium salt solution with an alkali sulfate salt solution to form a reaction mixture in a continuously operating mixing reactor, in which shear, displacement and frictional forces of intermeshing tools act at high relative speed on the reaction mixture formed, wherein at least some of said intermeshing tools are mounted on at least one rotor which rotates at a rotational speed of from 2000 rpm to 8000, whereby resulting barium sulfate is precipitated,
   wherein a wetting agent or a dispersing agent is added during or after precipitation of the resulting barium sulfate and
   after passage of the reaction mixture through the reactor, separating and drying the resulting barium sulfate;
   wherein the concentration of barium salt and sulfate in the salt solutions is at least 80% of the maximum possible concentration.

2. A method according to claim 1, wherein the concentration of barium salt and sulfate in the salt solutions is at least 90% of the maximum possible concentration.

3. A method according to claim 1, further comprising washing the separated barium sulfate at least once with water before drying.

4. A method according to claim 1, wherein the barium sulfate is precipitated at a temperature between 0° C. and 100° C.

5. A method according to claim 4, wherein the barium sulfate is precipitated at a temperature between 20° C. and 50° C.

6. A method according to claim 1, wherein the reaction mixture has a residence time in the mixing reactor in the millisecond range.

7. A method according to claim 1, wherein said barium salt solution and said alkali sulfate solution are aqueous solutions.

8. A method according to claim 1, wherein the barium salt solution is a solution of barium chloride.

9. A method according to claim 8, wherein the barium chloride solution has a BaCl$_2$ concentration of at least 0.9 mole/liter.

10. A method according to claim 1, wherein the alkali sulfate solution is a solution of sodium sulfate.

11. A method according to claim 10, wherein the sodium sulfate solution has a Na$_2$SO$_4$ concentration of at least 0.9 mole/liter.

12. A particulate, coated BaSO$_4$, comprising a wetting agent or a dispersing agent, wherein at least 95% of the particles have a primary grain diameter≦0.1 μm, produced according to the method of claim 1.

13. A particulate, coated BaSO$_4$ according to claim 12, wherein at least 99% of the particles have a primary grain diameter≦0.1 μm.

14. A particulate, coated BaSO$_4$ according to claim 13, wherein 100% of the particles have a primary grain diameter≦0.1 μm.

15. A plurality of coated BaSO$_4$ particles comprising a wetting agent or a dispersing agent, wherein at least 95% of the particles have a primary grain diameter<0.1 μm, produced according to the method of claim 1.

16. A plurality of coated BaSO$_4$ particles according to claim 15, wherein at least 99% of the particles have a primary grain diameter≦0.1 μm.

17. A plurality of coated BaSO$_4$ particles according to claim 15, wherein 100% of the particles have a primary grain diameter≦0.1 μm.

* * * * *